United States Patent [19]

Fountain

[11] Patent Number: 5,269,979
[45] Date of Patent: Dec. 14, 1993

[54] METHOD FOR MAKING SOLVENT DILUTION MICROCARRIERS

[75] Inventor: Michael W. Fountain, Knoxville, Tenn.

[73] Assignee: Fountain Pharmaceuticals, Inc., Largo, Fla.

[21] Appl. No.: 882,801

[22] Filed: May 14, 1992

Related U.S. Application Data

[63] Continuation of Ser. No. 460,838, Jun. 8, 1989, Pat. No. 5,133,965, which is a continuation-in-part of Ser. No. 204,214, Jun. 8, 1988, abandoned.

[51] Int. Cl.$^5$ .................. A61K 9/12; A61K 9/127; B01J 13/02
[52] U.S. Cl. ........................ 264/4.6; 264/4.1; 424/450
[58] Field of Search ............... 424/450; 264/4.1, 4.6

[56] References Cited

U.S. PATENT DOCUMENTS

| | | | |
|---|---|---|---|
| 3,639,257 | 2/1972 | Harbort | 252/316 |
| 3,691,090 | 9/1972 | Kitajima et al. | 252/316 |
| 3,804,776 | 4/1974 | Yazawa et al. | 252/316 |
| 3,943,063 | 3/1976 | Morishita et al. | 252/316 |
| 3,993,754 | 11/1976 | Rahman et al. | 424/177 |
| 4,078,052 | 3/1978 | Papahadjopoulos | 424/36 |
| 4,188,447 | 2/1980 | Ehlenz | 428/310 |
| 4,217,344 | 8/1980 | Vanlerberghe et al. | 424/60 |
| 4,298,594 | 11/1981 | Sears et al. | 424/19 |
| 4,308,166 | 12/1981 | Marchetti et al. | 252/316 |
| 4,356,167 | 10/1982 | Kelly | 424/38 |
| 4,377,567 | 3/1983 | Geho | 424/1 |
| 4,389,330 | 6/1983 | Tice et al. | 427/213.36 |
| 4,485,054 | 11/1984 | Mezei et al. | 264/4.6 |
| 4,505,935 | 3/1985 | Larsson | 514/779 |
| 4,508,703 | 4/1985 | Redziniak et al. | 424/38 |
| 4,515,736 | 5/1985 | Deamer | 264/4.3 |
| 4,522,803 | 6/1985 | Lenk et al. | 424/1.1 |
| 4,532,123 | 7/1985 | Gardner | 264/4.1 X |
| 4,551,288 | 11/1985 | Kelly | 264/4.6 |
| 4,557,935 | 12/1985 | af Ekenstam et al. | 424/130 |
| 4,565,696 | 1/1986 | Heath et al. | 424/88 |
| 4,588,578 | 5/1986 | Fountain et al. | 424/1.1 |
| 4,599,226 | 7/1986 | Fox, Jr. et al. | 424/27 |
| 4,608,211 | 8/1986 | Handjani et al. | 264/4.6 |
| 4,610,868 | 9/1986 | Fountain et al. | 424/1.1 |

(List continued on next page.)

FOREIGN PATENT DOCUMENTS

| | | |
|---|---|---|
| 0158441 | 10/1985 | European Pat. Off. |
| 0186542 | 7/1986 | European Pat. Off. |
| 0249561 | 12/1987 | European Pat. Off. |
| 8500515 | 2/1985 | World Int. Prop. O. |
| 8804573 | 6/1988 | World Int. Prop. O. |
| 8901790 | 3/1989 | World Int. Prop. O. |

OTHER PUBLICATIONS

Derwent Abstract, 86-171194/27 (corresponding to EP 0186542).

A. Bangham, M. Standish, and J. Watkins, "Diffusion of Univalent Ions Across the Lamellae of Swollen Phospholipids," 13 *J. Mol. Biol.*, 238-252 (1965) (United Kingdom).

S. Batzri and E. Korn, "Single Biolayer Liposomes Prepared Without Sonication," 298 *Biochimica et Biophysica Acta* 1015-1019 (1973) (The Netherlands).

J. Brunner, P. Skrabal, and H. Hauser, "Single Bilayer Vesicles Prepared Without Sonication Physico-Chemical Properties," 455 *Biochimica et Biophysica Acta* 322-331 (1976) (The Netherlands).

(List continued on next page.)

Primary Examiner—Robert L. Stoll
Assistant Examiner—Daniel S. Metzmaier
Attorney, Agent, or Firm—Richards, Medlock & Andrews

[57] ABSTRACT

A method for forming vehicles for encapsulating passenger molecules which have been named solvent dilution microcarriers (SDMCs), and the products of this process, are disclosed which allows for immediate or delayed formation of the encapsulating vehicles following creation of a shelf-stable formed solution by dissolution of amphipathic bilayer-forming materials, appropriate solvent, and the passenger molecule, addition of aqueous solution, and further addition of solvent. The SDMCs are organized from the formed solution by dilution into an aqueous system, aerosolization, or rehydration in situ.

14 Claims, No Drawings

U.S. PATENT DOCUMENTS

| | | | |
|---|---|---|---|
| 4,619,794 | 10/1986 | Hauser | 264/4.1 |
| 4,619,795 | 10/1986 | Cohen | 264/4.6 |
| 4,685,911 | 8/1987 | Konno et al. | 604/897 |
| 4,708,861 | 11/1987 | Popescu et al. | 424/1.1 |
| 4,717,676 | 1/1988 | Wagner et al. | 436/501 |
| 4,721,612 | 1/1988 | Janoff et al. | 424/1.1 |
| 4,731,210 | 3/1988 | Weder et al. | 264/4.3 |
| 4,737,323 | 4/1988 | Martin et al. | 264/4.3 |
| 4,752,572 | 6/1988 | Sundberg et al. | 435/7 |
| 4,755,388 | 7/1988 | Heath et al. | 424/450 |
| 4,769,028 | 9/1988 | Hoffmann et al. | 424/443 |
| 4,783,402 | 11/1988 | Kokusho et al. | 435/52 |
| 4,797,284 | 1/1989 | Loper et al. | 424/449 |
| 4,804,539 | 2/1989 | Guo et al. | 424/450 |
| 4,808,402 | 2/1989 | Leibovich et al. | 424/423 |
| 4,810,499 | 3/1989 | Nuwayser | 424/448 |
| 4,812,407 | 3/1989 | Buchmann et al. | 435/291 |
| 4,839,175 | 6/1989 | Guo et al. | 424/450 |
| 4,921,757 | 5/1990 | Wheatley et al. | 428/402.2 |
| 4,959,341 | 9/1990 | Wallach | 502/404 |
| 4,975,421 | 12/1990 | Williams et al. | 514/54 |
| 5,000,958 | 3/1991 | Fountain et al. | 424/450 |
| 5,141,674 | 8/1992 | Leigh | 424/450 X |
| 5,154,930 | 10/1992 | Popescu et al. | 424/450 X |

OTHER PUBLICATIONS

Z. Chowhan, T. Yotsuyanagi, and W. Higuchi, "Model Transport Studies Utilizing Lecithin Spherules," 266 *Biochim. Biophys. Acta* 320–342 (1972) (The Netherlands).

D. Deamer and A. Bangham, "Large Volume Liposomes By An Ether Vaporization Method," 443 *Biochimica et Biophysica Acta* 629–634 (1976) (The Netherlands).

M. Mezei and V. Gulasekharam, "Liposomes–A Selective Drug Delivery System For the Topical Route of Administration," 26 *Life Sciences* 1473–1477 (1980) (United States).

F. Szoka, Jr. and D. Papahadjopoulos, "Comparative Properties and Methods of Preparation of Lipid Vesicles (Liposomes)," 9 *Ann. Rev. Biophys. Bioeng.* 467–508 (1980) (Palo Alto, Calif., USA).

D. Papahadjopoulos and J. Watkins, "Phospholipid Model Membranes–II. Permeability Properties of Hydrated Liquid Crystals," 135 *Biochim. Biophys. Acta* 639–652 (1967) (The Netherlands).

D. Papahadjopoulos and N. Miller, "Phospholipid Model Membranes–I. Structural Characteristics of Hydrated Liquid Crystals," 135 *Biochim. Biophys. Acta*, 624–638 (1967) (The Netherlands).

D. Papahadjopoulos, W. Vail, K. Jacobson, and G. Poste, "Cochleate Lipid Cylinders: Formation by Fusion of Unilamellar Lipid Vesicles" 394 *Biochimica et Biophysica Acta* 438–491 (1975).

F. Szoka, Jr. and D. Papahadjopoulos, "Procedure for preparation of Liposomes with Large Internal Aqueous Space and High Capture by Reverse-Phase Evaporation," 75 *Proc. Natl. Acad. Sci. USA* 9 pp. 4194–4198 (Sep., 1978) (United States).

O. Zumbuehl and Hans George Weder, "Liposomes of Controllable Size in the Range of 40 to 180 nm by Defined Dialysis of Lipid/Detergent Mixed Micelles," 640 *Biochimica et Biophysica Acta* 252–262 (1981) (The Netherlands).

METHOD FOR MAKING SOLVENT DILUTION MICROCARRIERS

RELATED APPLICATION

This is a continuation of application Serial No. 460,838 filed Jun. 8, 1989 now U.S. Pat. No. 5,133,965, which is a continuation-in-part of application Ser. No. 204,214 filed Jun. 8, 1988 (now abandoned).

TECHNICAL FIELD

This invention relates to the art of enclosing passenger molecules in a amphipathic carrier structure.

BACKGROUND OF THE INVENTION

There have been numerous attempts in the prior art to develop lipid-based vesicles which are capable of entrapping various materials of interest ("passenger molecules"). The known methods have generally resulted in generally spherical vesicles known as liposomes which are composed of a lipid bilayer having an inner space in which the entrapped material is held. These vesicles have been formed by methods employing mechanical agitation, for example, sonication or extrusion. After lipids in organic solvents were mixed, the resulting mixture was dried, followed by mechanical agitation and rehydration with the passenger molecule to be entrapped to encourage the lipid bilayer to enclose around the passenger molecule.

The liposomes formed by this method were generally heterogeneous in size and difficult to sterilize for in vivo applications. The stability or shelf-life of these liposomes was often very limited. The entrapment efficiency of passenger molecules was generally limited. The methods required, in general, toxic nonbiocompatible solvents. The prior procedures were not applicable to aerosolization or formation of liposomes in situ. The vehicles formed by this method generally could be sterilized only by filtration as they exhibited heat lability. Moreover, prior methodology was not acceptably adaptable to the entrapment of certain passenger molecules.

SUMMARY OF THE INVENTION

It has now been found that an amphipathic vehicle (hereinafter referred to as "Solvent Dilution MicroCarriers" or "SDMCs") can be made using a method which leads to entrapping the passenger molecule in the bilayer itself, or in association with a component of the bilayer, rather than inside the space created by a spherical bilayer. In this method, a solvent is mixed with an amphipathic material and a passenger molecule. A small amount of water is then added to form a turbid solution. Additional solvent is then added to form an optically clear solution, also referred to as the "formed solution." An organization step is performed either immediately or at a time remote from the previous steps. The organization may involve aerosolization, dilution into aqueous materials or drying and rehydrating. The amphipathic vehicles or solvent dilution microcarriers (SDMCs) are formed upon employment of the organization method. The vehicles formed by this method exhibit substantial size homogeneity and are capable of being sterilized by sterile filtration, heating or u.v. irradiation.

The process may be put on hold after the formed solution is made and that solution held until it is desired to perform the organization step.

The SDMCs formed by this new method are unique in that they entrap a wide range of passenger molecules. The SDMCs have a wide range of applications. Aerosols containing SDMCs may be advantageously applied to large surface areas, such as for example when the passenger molecule is a pesticide. On the other hand, aerosols are also applicable to delivery of medicaments and cosmetics such as antibiotics or hair sprays. The methodology of this invention is also useful for SDMC formation in situ. The formed solution or SDMCs may be adsorbed on a surface such as bandage material and dried. Hydration allows the SDMC to deliver the passenger molecule to the desired site.

A sustained-release wound dressing material comprised of a foam bandage material and SDMCs has also been found.

DETAILED DESCRIPTION OF THE INVENTION

In the examples which follow, Solvent Dilution Microcarriers (SDMCs) were prepared by solubilizing at least one amphipathic material such as a surfactant (for example a biocompatible surfactant with good miscibility such as, but not limited to, Tween, Triton, sodium dodecyl sulfate (SDS), sodium laurel sulfate, and sodium octyl glucoside), a phospholipid, a mixture of phospholipids, polar lipids, sterols, sterol esters, neutral lipids, fatty acids, or other bilayer forming material into an appropriate solvent along with a passenger molecule (a material intended to solubilize in SDMCs). Various mixtures of amphipathic materials may be used. In some cases, it is convenient to select a commercial preparation of phospholipids. A preparation comprising about 75–97% mixed soy phosphatides may be used. For examples, commercial preparations of 75–80% mixed soy phosphatides, the remaining percentage being soy oils and preparations comprising 95–97% mixed soy phosphatides, the remaining percentage being soy oils are available. Commercial preparations having these characteristics are sold, for example, under the trade designations "Alcolec S", "Alcolec X-tra A" and "Alcolec LKE." The appropriate solvent is selected from those able to solubilize both the amphipathic material(s) and the passenger molecules. Generally, the most preferable solvent is a low molecular weight hydrocarbon such as ethanol, propanol, butanol, isopropanol, chloroform, acetone, methylene chloride or propyl glycol and the like. In addition, the solvent must be appropriate for the particular intended use of the SDMCs. If the SDMCs are to be employed in vivo such as for example in an intravenous admixture (i.v. admixture), the solvent must be utilizable without causing toxicity in that application and generally must be biocompatible and readily miscible. In other applications, such as pesticide applications, the toxicity of the solvent is not as critical, but volatility becomes of more import. It is desirable in such case that the solvent volatilize immediately upon aerosolization. For formation in situ, such as for example when bandage material is impregnated for later rehydration, it is important that the solvent be non-flammable-, that it volatilize quickly, and leave no residue in the matrix. Methylene chloride is one example of an appropriate solvent for such an application. Mixtures of solvents may be appropriate in some circumstances. The passenger molecule may be generally any material capable of being retained in a formed bilayer or associated with that bilayer. Passenger molecules such as antimicrobials, antiinflammatories, anti-parasitics, dyes, radiolabels, radio-opaque compounds, fluorescent compounds, immunomodulating compounds, peptides, proteins, glycoproteins, lipoproteins, hormones, neurotransmitters, tumorocidal agents, growth factors, toxins, analgesics, anesthetics, mono and polysaccharides, narcotics, catalysts and enzymes are examples of the classes of substances which may be utilized. It is most preferred that the passenger molecule be lipophilic, however hydrophilic materials may also be utilized if they are capable of forming an association with the bilayer (i.e., the polar head group of the lipids). Cosmetics or cosmetic ingredients such as hair sprays, colorants, dyes, and the like are often highly appropriate for encapsulation in an SDMC. Medicaments used in mouthwashes, throat sprays, antiseptic sprays and the like also may be candidates for SDMC encapsulation. Drugs or tumorocidal agents for i.v. admixture or other introduction method may be encapsulated in an SDMC utilizing the disclosed method. It is envisioned that SDMC vehicles containing toxic drugs may be effectively administered to a patient by coupling the SDMC to site-specific monoclonal antibodies, for example. In the alternative, the encapsulation alone may allow administration of certain drugs that could not be administered in unencapsulated form in an efficient or effective manner.

Following the mixing of the bilayer-forming material, passenger molecule, and solvent, water is added in the ratio of from about 4:1 (solvent to water) to about 10:1 (solvent to water), to form a turbid solution. Additional solvent is then added in the ratio from about 15:1 (solvent to water) to about 100:1 (solvent to water) or until the formed solution is optically clear. The additional solvent will generally be the same as used in the first step, but it may be a mixture of solvents or a different solvent which is appropriate to accomplish the desired result.

An organization step is done either immediately, or after storage of the formed solution for an indefinite period. The organization step may be aerosolization, dilution into an aqueous solution or drying and rehydrating. Aerosolization is performed simply by putting the material formed as described above into a sprayer or trigger pump such as would be commonly used for applying non-pressurized hair sprays, insecticides, and the like to other surfaces. Upon spraying the formed solution, it is mixed with air and the volatile solvent evaporates as the solution leaves the nozzle.

The dilution method of organization comprises diluting an aliquot of formed solution into water. Upon dilution, the SDMCs are formed. One preferred appropriate dilution ratio is 1 to 10 (from 1 part formed solution to 9 parts water). The dilution ratio may range from about 1 to 5 to about 1 to 100.

The drying and rehydrating form of organization may be done by putting the formed solution onto a surface such as a bandage gauze, tampon, foam dressing, contraceptive sponge and the like and allowing the solvent to evaporate off very quickly. Upon hydrating the impregnated- gauze, the SDMCs are formed in situ and can perform their function of transporting the passenger molecule to the appropriate site on a wound, for example.

The SDMC vehicles formed by this method may be evaluated by utilizing a light scattering technique to determine the presence of vesicles. This technique can also be used to estimate the size of the SDMCs. Various instruments are commercially available for the sizing and counting of cells or other particles. The Coulter particle analyzers available from Coulter Electronics, Hialeah, Fla. have been found useful in this regard. Specifically the Coulter NM4AM multi-angle submicron particle analyzer has been successfully employed. Vehicle size may also be estimated using standard column chromatography techniques. The SDMCs have also been analyzed by testing the efficacy of the SDMC preparation over standard commercial preparations of the passenger molecule. The SDMCs have been found to have successfully encapsulated the molecule of interest by utilizing standard tests for the efficacy of the passenger molecule. For example, pesticides may be tested for efficacy in killing insects and antibiotics for efficacy in standard microbiological assays.

It has been found that SDMCs exhibit substantial size homogeneity. The size is believed to be dependent on the passenger molecule and identity of the amphipathic materials utilized, but it has been demonstrated that within one preparation of SDMCs, the size range is very compact. This characteristic is believed to be important in several applications of SDMCs including in vivo drug delivery.

The SDMCs have also been tested to be stable to heat sterilization and cobalt irradiation sterilization, which widens their utility for uses where sterility is required.

The optically clear solution is shelf-stable for months which allows one to delay SDMC formation until a later date. The organization step may be performed by the end user in many applications such as pesticide application by aerosolization, among others.

A sustained-release wound dressing is disclosed which utilized SDMCs in a foam bandage material. The foam bandage material suitable for the invention is preferably a crosslinked foam consisting of a mixture of polyolefins and other polymers (usually aryl-containing polymers) to form a three-dimensional network. Examples of commercially available forms of this material are Hypol ® FMP 2002, marketed by W.R. Grace & Company (Lexington, Mass. 02173), and the Kontour sterile sponge, marketed by Winfield Laboratories, Inc. (P.O. Box 832616, Richardson, Tex. 75081). Other foam bandage material may be used as long as it is capable of loading the SDMCs and nontoxic to animals at the wound site and are preferably hydrophili, although they may be hydrophobic.

A method of wound treatment utilizing the sustained-release wound dressing is suitable for treating wounds that require at least about 30 minutes of therapy up to about seven days. The medicament is released slowly over the treatment time. A nonadherent dressing material may be applied to the wound prior to the foam bandage material.

The non-adherent dressing should be made from biocompatible synthetic or naturally occurring fibers arranged in a matrix having pores of a size large enough to allow the SDMCs to pass from the foam dressing to the wound site. Such wound dressings are available commercially from several companies. An example of this type of dressing is N-Terface ® interpositional surfacing material which is available from Winfield Laboratories, Inc. in Richardson, Tex. 75083.

The following examples are intended to illustrate the invention, but is to be understood that various modifications thereof will be apparent to one skilled in the art and it is intended to cover such modifications as fall within the scope of the appended claims and that the examples are submitted for the purpose of providing a better understanding of the present invention and are not to be construed as limiting the scope thereof.

EXAMPLE 1

SDMCs Containing Gentamicin

A sample of 200 mg of soy lecithin was solubilized at room temperature with 20 mg of gentamicin base in 5 ml of absolute ethanol. Two ml of water was added to the solution which resulted in a turbid suspension. Six ml of absolute ethanol was added to the suspension yielding an optically clear solution. SDMCs were formed by dilution of 1 ml of final solution into 10 ml of aqueous solution. The resulting opalescent suspension of SDMCs was characterized by chromatographic separation over a Sepharose CL 4B column. The SDMCs were found to entrap virtually 100% of the starting gentamicin base as determined by a generally accepted bioassay of SDMCs containing gentamicin base to inhibit the growth of *E. coli*.

EXAMPLE 2

SDMCs Containing Vitamin A

A sample of 1100 mg of soy lecithin was solubilized at room temperature with 10 mg of retinol (vitamin A) in 2.5 ml of absolute ethanol. One ml of water was added to the solution which resulted in a turbid (cloudy) suspension. Three ml of absolute ethanol was added to the suspension yielding an optically clear solution. SDMCs were formed by dilution of 1 ml of final solution into 10 ml of aqueous solution.

EXAMPLE 3

SDMCs Containing Vitamin E

The procedure in Example 2 was followed except that vitamin A was replaced with vitamin E (α-tocopherol).

EXAMPLE 4

SMCs Containing Vitamin D2

The procedure in Example 2 was followed except that vitamin A was replaced with vitamin D2 (ergocalciferol).

EXAMPLE 5

SDMCs Containing Vitamin D3

The procedure in Example 2 was followed except that vitamin A was replaced with vitamin D3 (cholecalciferol).

EXAMPLE 6

SDMCs Containing Vitamin K

The procedure in Example 2 was followed except that vitamin A was replaced with vitamin K (2-methyl-3 phytyl-1,4-naphthoquinone, 3 phytylmenadione).

EXAMPLE 7

SDMCs Containing Sterols

The procedure in Example 2 was followed except that vitamin A was replaced with sterol (cholesterol).

EXAMPLE 8

SDMCs Containing Pesticides

A sample 1 g of soy lecithin was solubilized into a 300 ml solution (petroleum distillate) containing 0.2% w/v mixed pyrethrins and 2.0% w/v piperonyl butoxide. Twenty ml of water was added to the solution which resulted in a turbid (cloudy) suspension. To the suspension was added 300 ml of petroleum distillates which resulted in an optically clear solution. SDMCs were formed by aerosolization of solution into air using a trigger pump and by dilution of 1 ml of solution into 10 ml of water. The efficacy of these preparations was demonstrated by their ability to kill fleas, ants, and paper wasps when SDMCs were aerosolized using a trigger sprayer or when the solution was directly applied onto the insects.

EXAMPLE 9

SDMCs as Animal Dips

The procedure in Example 8 was followed except that piperonyl butoxide and pyrethrins were replaced with malathion. The resulting solution upon dilution (200 ml into 70 liters of water) resulted in a turbid solution which was used as a flea dip for dogs.

EXAMPLE 10

SDMCs as Plant Insecticide Sprays

The procedure in Example 8 was followed except that the starting concentration of piperonyl butoxide was 0.2% w/v and mixed pyrethrins 0.02% w/v. The resulting solution was proven to be insecticidal and did not injure plant leaves upon aerosolization to form SDMCs.

EXAMPLE 11

SDMCs Containing Peppermint Oil

A sample of 200 mg of soy lecithin was solubilized in 5 ml of peppermint oil (1% w/v solution) in absolute ethanol. One-half ml of water was added to solution which became turbid. The turbid suspension was solubilized by addition of 5 ml of absolute ethanol. Upon dilution 1:10 to water, an opalescent suspension of SDMCs resulted. The entrapment of peppermint oil was demonstrated by a taste test evaluation comparing the SDMCs to peppermint oil in solvent alone. The evaluation demonstrated a prolonged peppermint taste resulted from the use of SDMCs as compared to peppermint oil in solvent alone.

EXAMPLE 12

SDMCs Containing Vanilla

The procedure in Example 11 was followed except that peppermint oil was replaced by vanilla.

EXAMPLE 13

SDMCs Containing Pineapple Oil

The procedure in Example 11 was followed except that peppermint oil was replaced by pineapple oil.

EXAMPLE 14

SDMCs Containing Anise Oil

The procedure in Example 11 was followed except that peppermint oil was replaced by anise oil.

EXAMPLE 15

SDMCs Containing Orange Extract

The procedure in Example 11 was followed except that peppermint oil was replaced by orange extract.

EXAMPLE 16

SDMCs Containing Facial Cleansers

A sample of 200 mg of soy lecithin was solubilized with 10% w/v salicylic acid in 10 ml isopropyl alcohol. One ml of water was added to form a cloudy turbid suspension. Ten ml of isopropyl alcohol was added to the suspension which resulted in an optically clear solution. The solution (1 ml) was diluted into 10 ml of water resulting an opalescent suspension of SDMCs. The material was tested and found to demonstrate good contact time on skin surfaces.

EXAMPLE 17

SDMCs Containing Fragrances

Ten ml of alcohol-based perfume was solubilized with 200 mg of soy lecithin. One ml of water was added to solution resulting in a cloudy suspension. The suspension was solubilized by addition of 10 ml of absolute ethanol. SDMCs were formed by aerosolization using a trigger pump and by dilution 1:10 w/v in water. The SDMCs were tested by application to skin. It was found that fragrances could be detected by olfaction longer than standard preparations were so detectable.

EXAMPLE 18

SDMCs in Mouthwash

A sample of 300 mg of soy lecithin was solubilized in 30 ml of 70% w/v alcohol 38B containing 1.0% of oil of peppermint w/v. Three ml of water was added to the solution which resulted in a cloudy suspension. Thirty ml of 70% v/v alcohol 38B was added to suspension to form a solution. The mouthwash was tested by dilution in saliva upon gargling and by prior dilution 1:10 v/v of solution into water prior to gargling. The results demonstrated prolonged contact of SDMCs in mouth by taste of peppermint oil SDMCs when compared with mouthwash lacking SDMCs.

EXAMPLE 19

SDMCs as Hair Spray

To a 20 ml sample of a commercially available liquid hair spray was added 200 mg of soy lecithin. To the solution was added 2 ml of water resulting in a cloudy suspension. Twenty ml of commercially available liquid hair spray was added to suspension resulting in an optically clear solution. The solution was aerosolized using a finger pump and found effective as a hair spray.

EXAMPLE 20

Stability of SDMC Forming Solution

An optically clear solution formed as describe in Example 8 was stored at room temperature for 15 months and demonstrated an optically clear solution which, upon aerosolization or dilution into water resulted in an opalescent SDMC suspension which was active as an insecticide in killing ants, fleas, and paper wasps.

EXAMPLE 21

SDMCs in A Gauze Pad Dressing

The procedure in Example 1 was followed resulting in a clear solution which, upon dilution, formed an opalescent suspension of SDMCs entrapping gentamicin base. The suspension was aerosolized onto gauze pads. SDMCs formed on the surface and were allowed to dry. After drying, the bandage material was tested in bioassays using generally accepted laboratory procedures and it was found that there was active gentamicin base. The bandage material onto which SDMCs were aerosolized was saturated with water and allowed to stand. The water was removed and yielded an opalescent suspension of SDMCs which contained active gentamicin base when tested by bioassay with *E. coli.*

EXAMPLE 22

Antimicrobial SDMCs in Tampons

The procedure would be the same as employed in Example 21, except that tampons would be used rather than gauze pads.

EXAMPLE 23

Entrapment of PCMX (Poly-Chloro-Meta-Xylenol)

To 185 ml of ethanol was added 18.5 ml of water. 295 ml. of Tween detergent was added to ethanol/water mixture. 50 ml soy lecithin was added to the above solution. 165 grams of PCMX was added and stirred to form a yellow clear solution. The clear yellow PCMX solution was diluted 1:10 in water. This dilution yielded an optically turbid solution of solvent dilution microcarriers containing solubilized PCMX.

EXAMPLE 24

Antimicrobial Mouthwash

To 200 ml of a 70% ethanol-containing commercial mouthwash base was added a solution containing 45 ml of ethanol, 20 grams of soy lecithin, 0.5 grams of PCMX and 5 ml of water. The solutions were mixed and yielded a final solution containing 0.2% PCMX. The antimicrobial activity of the resulting mouthwash was tested and found to be increased over both commercial mouthwash and mouthwash lacking SDMCs but containing PCMX.

EXAMPLE 25

Intravenous Admixture for Tetrachlordecaoxid

An intravenous solution for injection (i.v. admixture) was prepared. Into 50 ml of ethanol was solubilized $6.9\times10^8$ I.U. of Tetrachlordecaoxid (TCDO) and 5 grams of soy lecithin. Water (5 ml) was added to the ethanol solution to form a turbid solution. 50 ml of ethanol was added to clarify the turbid solution. SDMCs were prepared by dripping TCDO solution into 1 liter of 0.9% w/v saline. The SDMCs which resulted by dispersion into saline were analyzed by using light scattering to detect the presence of the vesicles. A Coulter NM4AM multi-angle submicron particle analyzer (Coulter Electronics, Hialeah, Fla.) was utilized according to the manufacturer's instructions for the light scattering technique. Antimicrobial activity was accessed and found to be present at least 4 days after dilution using generally accepted laboratory techniques with *E. coli.*

EXAMPLE 2

Gentamicin In An i.v. Admixture

An i.v. admixture of gentamicin was prepared as described in Example 25 by substituting 0.1 grams gentamicin for TCDO.

EXAMPLE 27

Gentamicin SDMC's in Foam Wound Dressing

To a solution of 50 ml of methylene chloride was added 10 grams of soy lecithin, 0.1 grams of gentamicin base and 5 ml of water. 50 ml of additional methylene chloride was added. Onto a commercial surgical foam wound bandage was poured the above solution and the methylene chloride allowed to evaporate. The sponge material containing the SDMC forming solution was mixed with water and evaluated using light scatter as described in Example 25. The size of SDMC's which emerged from foam material was from about 190 to 200 mm (mean size 180). The foam material with SDMC forming solution was tested in bioassays using *E. coli* and it was found that there was active gentamicin base as determined by standard antimicrobial test procedures.

EXAMPLE 28

Silver Sulfadiazene SDMC's in Foam Wound Dressing

The procedure as in Example 27 was repeated with the exception that silver sulfadiazene (1% w/w) was added in place of gentamicin base. The mean particle size was found to be about 210 nm.

EXAMPLE 29

TCDO in a Foam Wound Dressing $6.9\times10^7$ I.U. TCDO was impregnated into foam would dressing as described for gentamicin in Example 27. The mean size was found to be 220 nm.

EXAMPLE 30

SDMC containing Methoprene in Foam Wound Dressing

The procedures in Example 27 was repeated with exception that methoprene (0.2% w/w) replaced gentamicin.

EXAMPLE 31

Fibronectin in Foam Wound Dressing 10 grams soy lecithin and 50 mg of fibronectin was impregnated into foam as in Example 27. SDMC's were consistent with the size structure of other SDMCs, having a mean size of 190 nm.

EXAMPLE 32

Stability of Passenger Molecule Activity Over Time

Antibacterial activity of the 2.5% PCMX containing SDMCs after thirty days room temperature storage and 1 hour at 70° C. was testing by spotting 20 ul formed solution in the center of a lawn of *E. coli* strain Y1089. (The lawn was created by growing Y1089 at 30° C. in Luri Broth [LB] broth until an optical density of 0.1 at 600 nm was achieved). Twenty ul of the *E. coli* suspension was spotted in the center of a LB plate and spread with a sterile inoculating loop. Plates to be tested were held for 18 hours at 30° C. until the antibacterial effects could be seen and measured in the confluent lawn of *E. coli*.

It was shown that the small amount of residual solvent and other components used to entrap (encapsulate) PCMX had no inhibitory effect on microbial growth (no zone of growth inhibition was seen).

A 3% solution of non-encapsulated PCMX was spotted in a like manner and was found to create a 8 mm zone of growth inhibition compared to SDMC. Encapsulated PCMX created a 25 mm zone. No significant reduction in the ability of encapsulated PCMX to inhibit bacterial growth was noted when procedures using 30 day old or heat treated SDMCs (30 day old SDMCs heated at 70° C. for one hour) were compared.

EXAMPLE 33

Comparison of PCMX SDMC Activity to a Commercial Preparation of PCMX

The antibacterial activity of SDMCs containing PCMX (2.5%) as a passenger molecule was compared against a commercial preparation of PCMX (Ultradex (Dexide Inc.) (3%)). Both solutions were diluted 1:2 v/v in LB broth using standard bacteriostatic and bacteriocidal assay techniques (1 ml total volume). After dilution of the two antimicrobial preparations, 0.1 ml of a 0.1 O.D. solution of *E. coli* Y1089 was added to each dilution tube. All tubes were incubated at 30° C. for 18 hours. After the incubation, each dilution was tested for microbial growth by removing a small amount of broth using a sterile inoculating loop and streaking on a LB plate. After incubating the plates for 18 hours at 30° growth inhibition at each dilution was determined by examining the plates for growth of Y1089. Bacterial growth inhibition by Ultradex (3%) stopped a dilution of 1:64 v/v. The 2.5% PCMX SCMC preparation inhibited growth up to a dilution of 1:1024. Therefore, the preparation has 16–32X better bacteriocidal activity than the Ultradex 3% solution.

EXAMPLE 34

A mouthwash was formulated employing 2.5% PCMX. Antibacterial activity of the mouthwash without PCMX was tested and no inhibition of *E. coli* was found using the standard plate inhibition assay, even though the mouthwash contained 70% ethanol. A 2.0% solution of PCMX in the mouthwash was prepared and upon testing found to achieve a zone of 19 mm compared to a 25 mm zone which was created by only a 0.2% solution of a SDMC encapsulated preparation.

EXAMPLE 35

A new encapsulated 5% PCMX suspension was tested using the *E. coli* plate inhibition assay. The control plate showed no zone of bacterial inhibition compared to the free PCMX that had a zone approximately 20 mm. The 5% free suspension did not achieve a complete inhibition of bacteria within the 20 mm zone. The SDMC preparation in contrast, showed complete inhibition of bacterial growth with a 35 mm zone due to the solubilization of the agent and even distribution over the surface.

EXAMPLE 36

SDMC Size Distribution, Time and Heat Stability

The size distribution of solvent dilution microcarriers containing 2.5% PCMX was tested using a Coulter NM4A multi-angle sub micron particle analyzer as previous described. Batch A was prepared on the same day as Batch B and as can be seen in Table I, the size of the SDMCs is fairly homogenous and stable over time and after heating at 70° C. for 1 hour.

TABLE I

| SDMC | Size (Day 1) | Size (Day 30) | Size Day 30 after Heating at 70° C. for 1 hour |
|---|---|---|---|
| Batch A | 130-230 nm (mean 180) | 105-190 nm (mean 169) | 100-140 hours (mean 123) |
| Batch B | 180-300 nm (mean 227) | NT | NT |

NT = Not Tested

EXAMPLE 37

SDMCs in a Vaginal Sponge Contraceptive

SDMCs would be prepared as described in Example 2, except that estrogen or estrogen-like compounds would be utilized as the passenger molecule. In the alternative, a spermicidal agent such as nonoxynol-9 could be employed as the passenger molecule.

EXAMPLE 38

Sustained Release of Tobramycin SDMC From Foam Wound Dressing

To a solution of 75 ml of dichloromethane was added 10 grams of soy lecithin and 200 mg of tobramycin sulfate in 5 ml of water. The solution was mixed by shaking and 4 ml were applied onto each side of the 1"×1" foam bandage material and allowed to air dry. Four ml of a solution comprising 20 mg of tobramycin sulfate in 8 ml of water was applied onto each side of 10 additional foam bandage material pieces (1"×1") and allowed to air dry. The foam bandage pieces were placed onto a grid support, wetted with 5 ml of water and 2 ml of eluent was collected which flowed through the foam dressing and into the underlying receptacle. The foam dressings were wetted subsequent times and 2 ml of eluent was collected. The antimicrobial activity of eluent was determined using standard antimicrobial inhibition assays using $E.\ coli$ strain Y-1089. The results as shown in Table II.

TABLE II

Release of Tobramycin From Foam Dressing

| Collection Point | Aqueous Tobramycin | SDMC Entrapped Tobramycin |
|---|---|---|
| | Concentration mg per 2 ml | |
| 1 | 19.0 | 0.50 |
| 2 | 0.50 | 0.50 |
| 3 | 0.10 | 0.50 |
| 4 | 0.10 | 0.55 |
| 5 | less than 0.10 | 0.45 |
| 6 | N.D.* | 0.45 |
| 7 | N.D. | 0.50 |
| 8 | N.D. | 0.50 |
| 9 | N.D. | 0.50 |
| 10 | N.D. | 0.45 |
| 11 | N.D. | 0.50 |
| 12 | N.D. | 0.45 |
| 13 | N.D. | 0.50 |
| 14 | N.D. | 0.45 |
| 15 | N.D. | 0.50 |
| 16 | N.D. | 0.50 |
| 17 | N.D. | 0.55 |
| 18 | N.D. | 0.50 |

*N.D. = Not Detected

EXAMPLE 39

Sustained Release of SDMC from Foam Wound Dressing

To a solution of 75 ml of dichloromethane was added 10 grams of soy lecithin and tracer amounts of $^{14}$C-Dipalmitoylphosphatidylcholine (DPPC) and 5 ml of water. The solution was mixed by shaking and 4 ml were applied onto each side of a 1"×1" foam bandage material and allowed to air dry. The foam bandages were placed onto a grid support, wetted with 5 ml of water and 2 ml of eluent was collected. Eluent samples were assayed by liquid scintillation counting techniques. The results demonstrated that uniform amounts (between 1-3%) of SDMCs were collected after each application of fluid. Results indicated that over 25 applications of fluid were required to exhaust the foam bandage of SDMCs.

EXAMPLE 40

Entrapment of Tobramycin in SDMC as It Elutes from Foam Wound Dressing

To a solution of 75 ml of dichloromethane was added 10 grams of soy lecithin (with tracer amounts of $^3$-Hphosphatidlylcholine) and 200 mg of tobramycin sulfate in 5 ml of water. The solution was mixed by shaking and 4 ml were applied onto each side of 1"×1" foam bandage material and allowed to air dry. The bandage materials were placed onto a grid support as in Example 1 and wetted with 5 ml of water. The eluents for the first nine wettings were discarded. After ten repeated wettings the eluent was collected and passed over a Sephadex G-150 column. The material which was excluded by the column and included by the column bed was assayed for tobramycin using standard antimicrobial assays with $E.\ Coli$ strain Y-1089. The material which was excluded was subjected to turbidity measurements and laser light scattering analysis. The sizes of the SDMCs were consistent with those previously observed between 0.15 m and 0.3 m and when assayed for tobramycin demonstrated that the antibiotic was indeed entrapped within the SDMCs which eluted from the foam bandage material. The included volume contained a small amount (less than 10% of the total tobramycin) which had either not been entrapped in SDMCs or had leaked out of SDMCs during transit from foam dressing or over the Sephadex column.

EXAMPLE 41

Stability of SDMC Encapsulated Materials As They Leave Foam Bandage Material

To a solution of 50 ml of dichloromethane was added 10 grams of soy lecithin, $6.9 \times 10^7$ I.U. of tetrachlordecaoxid ("TCDO") and 5 ml of water, 50 ml of additional dichloromethane was added and the resulting solution was mixed by shaking. Four ml of solution were applied onto each side of 1"×1" foam bandage material and allowed to air dry. Eight ml (4 ml onto each side) of a solution containing $5.0 \times 10^6$ I.U. of TCDO was applied onto an additional 1"×1" foam bandage material. The bandage materials were placed onto a grid support, wetted with 5 ml of water and 2 ml aliquots were collected from both the SDMC entrapped TCDO sponges and the sponges impregnated with TCDO alone. The aliquots were analyzed for antimicrobial activity immediately and stored at room temperature. At subsequent times (for 48 hours) aliquots were again assayed for TCDO activity. The results of the percentage of initial activity retained in each aliquot is shown in Table III.

TABLE III

| Stability of SDMC Entrapped TCDO Eluent From Foam Wound Bandage | | |
|---|---|---|
| Hours After Elution From Bandage | Percentage of Initial Antimicrobial Activity | |
| | TCDO | SMDC Entrapped TCDO |
| 0 | 100 | 100 |
| 2 | 40 | 85 |
| 4 | 20 | 65 |
| 8 | less than 1 | 60 |
| 24 | N.D.* | 55 |
| 36 | N.D. | 50 |
| 48 | N.D. | 50 |

*N.D. = Not Detected

EXAMPLE 42

Stability of SDMC Entrapped Material in Wet Bandage Environment

Foam bandage materials were prepared as in Example 4 (with either TCDO or SDMC entrapped TCDO). The foam bandage materials were placed onto a support grid and wet with 5 ml of water. Two ml eluent was collected at 4 hours and at 12-hour intervals for 4 days. The percentage of initial antimicrobial activity at each collection time was determined using standard antimicrobial assays. The results are shown in Table IV.

TABLE IV

| Stability of SDMC Entrapped TCDO In Wet Foam Wound Bandage | | |
|---|---|---|
| Hours After Wetting of Bandage | Percentage of 4 Hour Antimicrobial Activity | |
| | TCDO | SDMC Entrapped TCDO |
| 4 | 100 | 100 |
| 12 | less than 1 | 85 |
| 24 | N.D.* | 85 |
| 36 | N.D. | 85 |
| 48 | N.D. | 80 |
| 60 | N.D. | 80 |
| 72 | N.D. | 80 |
| 84 | N.D. | 80 |
| 96 | N.D. | 80 |

*N.D. = Not Detected

EXAMPLE 43

Stability of SDMCs to Osmotic Stress

To a solution of 25 ml of dichloromethane was added 5 grams of soy lecithin and 5 ml of water. Twenty-five ml of additional dichloromethane was added and the resulting solution was mixed by shaking. Four ml of solution were applied onto each side of 1"×1" foam bandage material and allowed to air dry. The foam bandages were placed onto a grid support, wetted with 5 ml of water and 2 ml aliquots of eluent were collected. To aliquots of eluent containing empty SDMCs were added increasing concentrations of sucrose or water, thus placing the SDMCs under increasing osmotic stress. Changes in SDMCs were monitored using laser light scattering analysis. Results are shown in Table V.

TABLE V

| Resistance of SDMCs to Increased Osmatic Stress | | |
|---|---|---|
| Micro Osmoles Osmatic Pressure | Percentage Sucrose | Size of SDMC NM |
| 539 | 0 | 125 ± 10 |
| 1,100 | 5 | 125 ± 20 |
| 2,156 | 10 | 150 ± 30 |
| 4,312 | 20 | 150 ± 30 |
| 6,624 | 30 | 150 ± 30 |
| 17,248 | 40 | 150 ± 30 |

EXAMPLE 44

Stability to SDMCs to Detergent Stress

SDMCs were prepared as in Example 6. To the eluent containing empty SDMCs were added either water or increasing amounts of Tween 20 (a commercial detergent). The effects or size of SDMCs was monitored using laser light scattering analysis. Results are shown in Table VI.

TABLE VI

| Resistance of SDMCs to Increased Detergent Concentration | |
|---|---|
| Percentage Volxme/Volume Tween 20 | Size of SDMCs (NM) |
| 0 | 190 |
| 0.15 | 190 |
| 0.3 | 190 |
| 0.75 | 190 |
| 1.2 | 205 |

EXAMPLE 45

Thermal Stability of Dry Tobramycin SDMC Forming Foam Wound Dressings

To a solution of 50 ml of dichloromethane was added 10 grams of soy lecithin and 200 mg of tobramycin sulfate in 5 ml of water. Fifty ml of additional dichloromethane was added and the solution was mixed by shaking. Eight ml of solution (4 ml per side) was added to a 1"×1" foam wound bandage material which was then allowed to air dry. The materials were analyzed for residual dichloromethane by high pressure liquid chromatography and found to contain no detectable residual dichloromethane. The 1"×1" foam wound materials were packaged individually in heat sealed bags and stored at room temperature for two months. At the end of two months the packages were opened and a representative first sample of SDMC-forming foam wound bandages were removed, placed onto grid supports, and wetted with 5 ml of water. Two ml of eluent containing SDMC-entrapped tobramycin were collected from the first sample. A second representative sample of SDMC-forming foam wound bandages were stressed by heating to +70° C. for three days. A third representative sample of SDMC-forming foam wound bandages were stressed by freezing at −70° C. for three days, then allowed to equilibrate to room temperature. These stressed foam wound dressings were then placed onto grid supports, wetted with 5 ml of water, and 2 ml of eluent containing SDMC-entrapped tobramycin was collected. All samples were subjected to analysis for tobramycin entrapped as explained in Example 3. The results are shown in Table VII.

TABLE VII

Effect of Thermal Stress of Tobramycin Entrapped in SDMC Forming Foam Wound Dressing

| Temperature | Concentration of Tobramycin Entrapped in SDMC (mg per ml) |
|---|---|
| Room Temperature | 0.5 mg/ml |
| +70° C. | 0.5 mg/ml |
| −70° C. | 0.5 mg/ml |

EXAMPLE 46

Thermal Stability of Dry Silver Sulfadiazine SDMC-Forming Foam Wound Dressing To a solution of 10% weight per volume soy lecithin in ethanol (192 ml) was added 418 grams of methyl paraben and mixed by shaking. To the resulting solution was added 4.8 grams of silver sulfadiazine and mixed by shaking. One-hundred and twenty ml of Tween 20 was added to the solution which was then mixed by shaking. Dichloromethane (720 ml) was then added to the solution and mixed by shaking. Sixteen ml of this solution was placed on each side of a 4"×4" foam wound bandage material. This was allowed to air dry. The 4"×4" foam wound material was cut into 1"×1" square pieces. One representative sample of 1"×1" pieces was placed onto a grid support and wetted with 5 ml of water. Two ml of eluent containing SDMC silver sulfadiazine was then collected A second representative sample of the 1"×1" pieces of foam wound material was stressed by heating to +70° C. for three days. A third representative sample of the 1"×1" piece was stressed by freezing at −85° C. for three days, then allowing equilibration to room temperature. These stressed foam wound dressings were then placed onto grid and treated as above Eluent was collected-after each of the ten applications of 2 ml of water to each 1"×1" square test piece. All samples were subjected to analysis for silver sulfadiazine antimicrobial activity using standard microbiological techniques. The results are shown in Table VIII.

TABLE VIII

Effect of Thermal Stress of Silver Sulfadiazine Entrapped in SDMC Forming Wound Dressing

| Temperature | Concentration of Silver Sulfadiazine Entrapped in SDMC Collection Point | |
|---|---|---|
| | First Elution | Tenth Elution |
| Room Temperature | 21 | 20 |
| −85° C. | 20 | 21 |
| +70° C. | 20 | 21 |

EXAMPLE 47

Sustained-Release of SDMC Entrapped Tobramycin from Wet Foam Wound Material Over Time Foam wound materials containing tobramycin sulfate were prepared as shown in Example 1. Once the materials were placed onto grid supports they were maintained at room temperature and covered with a foil wrap. Every 12 hours for nine days, 5 ml of water was applied onto the foam bandage materials and eluent was collected. Two ml samples containing SDMC-entrapped tobramycin were assayed for tobramycin antibiotic activity using standard antimicrobial assays. The results are shown in Table IX.

TABLE IX

Sustained Release of Tobramycin from SDMC Forming Wound Dressing

| Time (Days) | SDMC Tobramycin Concentration (μg/ml) |
|---|---|
| 0 | 400 |
| 0.5 | 410 |
| 1.0 | 415 |
| 1.5 | 415 |
| 2.0 | 415 |
| 2.5 | 405 |
| 3.0 | 405 |
| 3.5 | 390 |
| 4.0 | 400 |
| 4.5 | 405 |
| 5.0 | 405 |
| 5.5 | 410 |
| 6.0 | 405 |
| 6.5 | 410 |
| 7.0 | 410 |
| 7.5 | 410 |
| 8.0 | 415 |
| 8.5 | 405 |
| 9.0 | 410 |

EXAMPLE 48

Sustained Release of SDMC Entrapped Gentamicin From Wet Foam Wound Material Over Time Foam wound materials containing gentamicin sulfate were prepared as shown in Example 1. Once materials were prepared they were placed onto grid supports and maintained at room temperature. All were covered with a foil wrap. Every 12 hours for nine days, 5 ml of water was applied onto the foam bandage materials and eluent was collected. Two ml samples containing SDMC entrapped gentamicin were assayed for gentamicin antibiotic activity using standard antimicrobial assays. The results are shown in Table X.

TABLE X

Sustained Release of Gentamicin From Wet SDMC Forming Wound Dressing

| Time (Days) | SDMC Entrapped Gentamicin Concentration (μg/ml) |
|---|---|
| 0 | 200 |
| 0.5 | 200 |
| 1.0 | 205 |
| 1.5 | 205 |
| 2.0 | 205 |
| 2.5 | 205 |
| 3.0 | 200 |
| 3.5 | 175 |
| 4.0 | 190 |
| 4.5 | 200 |
| 5.0 | 200 |
| 5.5 | 200 |
| 6.0 | 200 |
| 6.5 | 205 |
| 7.0 | 195 |
| 7.5 | 200 |
| 8.0 | 200 |
| 8.5 | 200 |
| 9.0 | 205 |

EXAMPLE 49

Preparation and Sterilization of Polymyxin B SDMCs in Foam Wound Dressing

To a solution of 125 ml of dichloromethane was added 500,000 units (10 ml of aqueous solution) of polymyxin B. The resulting solution was mixed by shaking. To the solution was added 20 ml of soy lecithin (Alcolec x-tra A) and the resulting solution was mixed by shaking. Four ml of above solution was added to each side of a 1"×1" foam wound material which was allowed to air dry. The materials were placed into heat sealed pouches and sterilized by use of cobalt irradiation (3.2 megarads). The resulting materials were assayed by placing them onto grid supports, wetting with 5 ml [water] and collecting 2 ml of eluent containing SDMC entrapped polymyxin B. The eluent contained fully active entrapped antibiotic after irradiation as determined by use of standard antimicrobial-assay techniques.

EXAMPLE 50

Preparation and Sterilization of Kanamycin SDMCs in Foam Wound Dressing

To a solution of 125 ml of dichloromethane was added 1 gram of kanamycin sulfate in 10 ml of aqueous solution. To the resulting solution was added 20 ml of soy lecithin (Alcolec S). The solution was mixed by shaking. Four ml of the solution was applied to each side of a 1"×1" foam wound dressing, which was then allowed to dry. These materials were placed in foil heat sealed bags and subjected to sterilization by use of cobalt irradiation (3.2 megarads). The materials were assayed for antibiotic activity as described in Example 12. The eluent contained fully active entrapped antibiotic after irradiation by using standard antimicrobial assay techniques.

EXAMPLE 51

Sustained Release of SDMC Entrapped Silver Sulfadiazine From Wet Foam Wound Materials Over Time Foam wound materials were prepared as described in Example 9. Once the materials were placed onto grid supports, they were maintained at room temperature and covered with a foil wrap. Every 12 hours for seven days, 5 ml of water was applied onto the foam bandage materials and eluent was collected. Two ml samples containing SDMC entrapped silver sulfadiazine were assayed for silver sulfadiazine antimicrobial activity using standard microbiological techniques. The results are shown in Table XI.

TABLE XI

Sustained Release of Silver Sulfadiazine From Wet SDMC Forming Foam Wound Dressing

| Time (Days) | SDMC Entrapped Silver Sulfadiazine Concentration ($\mu$g/ml) |
| --- | --- |
| 0 | 18 |
| 0.5 | 20 |
| 1.0 | 20 |
| 1.5 | 19 |
| 2.0 | 20 |
| 2.5 | 20 |
| 3.0 | 21 |
| 3.5 | 20 |
| 4.0 | 19 |
| 4.5 | 20 |
| 5.0 | 21 |
| 5.5 | 20 |
| 6.0 | 21 |
| 6.5 | 20 |
| 7.0 | 20 |

EXAMPLE 52

Preparation and Sterilization of Cefoxitin Entrapped in SDMCs

To a solution of 15 ml of 10% (weight per volume) NaCl in water was added 4 grams of cefoxitin. The mixture was shaken and resulting SDMCs entrapping cefoxitin were sterilized using Cobalt irradiation (2.5 megarads). The SDMCs were assayed for cefoxitin antimicrobial activity using standard microbiological techniques and found to both entrap the cefoxitin and preserve its activity both during one week storage at 4° C. and through irradiation sterilization.

EXAMPLE 53

Preparation and Sterilization of Amakacin Entrapped in SDMCs

To a solution of 15 ml of 10% (weight per volume) soy lecithin (Alcolec LKE granules) was added 85 ml of 0.95% (weight per volume) NaCl in water containing 2 grams of amakacin sulfate. The mixture was shaken and resulting SDMCs entrapping amakacin were sterilized using cobalt irradiation (2.5 megarads). The SDMCs were assayed for amakacin antimicrobial activity using standard microbiological methodology and found to both entrap amakacin and preserve the activity of the antibiotic both during storage at 4° C. and through irradiation sterilization.

EXAMPLE 54

Preparation of Kanamycin Entrapped SDMCs

To a 40 ml solution of 0.05 potassium phosphate (pH 7.0) was added 1 gram of tobramycin sulfate. Three ml of a 10% (weight per volume) soy lecithin in ethanol solution was added to tobramycin containing solution. The resulting SDMC containing mixture was swirled to entrap tobramycin with SDMCs. To adjust volume 57 ml of 0.05 M potassium phosphate was added and resulting suspension was passed through a 0.45 %m filter into a sterile vial.

EXAMPLE 55

Preparation of a Stable Cyclosporin Admixture

To 2 ml of a 10% (weight per volume) soy lecithin in ethanol solution was added 3 mg of cyclosporin. The solution was mixed by swirling. To form SDMC 50 $\mu$l aliquot of above solution was mixed with 450 $\mu$l of water. The resulting SDMCs containing cyclosporin were analyzed using laser light scattering and found to be approximately 200 $\mu$m in diameter. The admixture was stored at room temperature for one year and subjected to testing as above. The results found no change in size (200 $\mu$m diameter) and no precipitation of cyclosporin in the admixtures during storage for one year.

EXAMPLE 56

Use of Novel Wound Dressing Package Containing Gentamicin Sulfate for Treatment of Soft Tissue Infections in Rats A model of soft tissue infection was established in Sprague Dawley rats. Rats were anesthetized and a 3×3 cm square of skin was excised from the back exposing paraspinus muscles. One-half ml of a suspension containing 1×10$^8$ cfu/ml of *Pseudomonas aeroginosa* was injected into the superficial facia of each paraspinus muscle for a total volume of 1 ml. Wounds were covered with a non-adherent dressing material (N-terface ® interpositioned surfacing material, available from Winfield Laboratories, Richardson, Tex. 75083) and either a foam wound material or a predryed foam wound dressing prepared by impregnation of a SDMC forming solution consisting of 0.5 grams of soy lecithin and 2 mg gentamicin sulfate applied onto 1"×1" foam material (prepared as described in Example 1). In all cases bandage materials were moistened with 5 ml of either sterile water for 40 rats, 5 ml of sterile water for rats receiving SDMC gentamicin (40 rats) or 5 ml of sterile water containing 330 μg of gentamicin sulfate (40 rats). Animals were redampened every 12 hours as above for a duration of three days. During the three-day study at 24-hour intervals, groups of ten rats were sacrificed and the paraspinus muscle harvested obtaining between 1.5 and 3 grams of tissue. Colony forming units (CFU) of P. aeroqinosa [per] 1 gram of muscle tissue was determined using standard microbiological techniques. The results for each treatment group are shown in Table XII.

TABLE XII

Treatment of Soft Tissue Infections with Gentamicin

| Treatment Groups | Hours after Treatment (percent of time 0 bacteria per gram of tissue) | | | |
|---|---|---|---|---|
| | 0 | 24 | 48 | 72 |
| Untreated Controls | 100 | >100 | >100 | >100 |
| Aqueous Gentamicin | 100 | >100 | >100 | >100 |
| SDMC Gentamicin | 100 | 45 | 2 | <0.01 |

EXAMPLE 57

Use of Novel Wound Dressing Package Containing Silver Sulfadiazine for Treatment of Soft Tissue Infection in the Rat A model of soft tissue infection was established in Sprague Dawley rats as described in Example 17. All animals were treated as described in Example 17 with the following exceptions. Treatment groups consisted of 1) animal receiving foam wound dressing (wet with sterile water), 40 animals, 2) animals receiving 3 grams of 1% silver sulfadiazine (30 mg) (Silvadene ® Cream) applied into the wound, scrubbed away and reapplied twice daily for three days (40 animals) and 3) animals receiving a pre-dried foam wound material impregnated with SDMC forming solution consisting of 30 mg of silver sulfadiazine and 0.5 grams of soy lecithin (prepared as described in Example 9). The results for each treatment group are shown in Table XIII.

TABLE XIII

Treatment of Soft Tissue Infections With Silver Sulfadiazine

| Treatment Groups | Hours after Treatment (percent of time 0 bacteria per gram of tissue) | | | |
|---|---|---|---|---|
| | 0 | 24 | 48 | 72 |
| Untreated Controls | 100 | >100 | >100 | >100 |
| Silvadene Cream | 100 | 68 | 40 | 22 |
| SDMC Silver Sulfadiazine | 100 | 40 | 12 | <0.01 |

EXAMPLE 58

Use of SDMC Entrapped Cefoxitin to Treat Fatal Bacteria Septicemia Resulting From Mixed Bacterial Peritonitis A model for fatal septicemia resulting from mixed bacterial infections were established in Sprague Dawley rats. Rats were anesthetized and a midline incision made into abdomen. The peritoneal cavity was irritated with a barium solution and 1 gram of human fecal material was implanted into the peritoneal cavity. Animals were surgically closed. Blood samples were removed from caudal vein at zero, four hours and subsequent 24-hour intervals for the duration of a four-day study. Infections were established in a group of 40 animals. In a group of ten animals, no treatment was initiated. In a group of ten animals, cefoxitin 1.5 mg/kg was administered i.m. at the time of surgical closure. In a group of ten animals, cefoxitin 1.5 mg/kg was administered into the peritoneal cavity at the time of surgical closure. In a group of ten animals, SDMC-entrapped cefoxitin 1.5 mg/kg was administered at the time of surgical closure. In a group of ten animals, empty SDMCs were administered i.p. at the time of surgical closure. The results of this study are shown in Table XIV.

TABLE XIV

Treatment of Fatal Septicemia Resulting From Mixed Bacterial Peritonitis

| Treatment Groups | Bacteria (cfw/ml) In Blood Per Ml Hours After Treatment | | | | |
|---|---|---|---|---|---|
| | 0 | 4 | 24 | 48 | 72 |
| Controls | 0 | $1 \times 10^4$ | $1 \times 10^7$ | $>1 \times 10^7$ | $>1 \times 10^7$ |
| Cefoxitin (i.m.) | 0 | $1 \times 10^3$ | $1 \times 10^4$ | $1 \times 10^4$ | $1 \times 10^4$ |
| Cefoxitin (i.p.) | 0 | $1 \times 10^3$ | $1 \times 10^4$ | $1 \times 10^4$ | $1 \times 10^4$ |
| SDMC cefoxitin (i.p.) | 0 | $>1 \times 10^1$ | $>1 \times 10^1$ | $>1 \times 10^1$ | $>1 \times 10^1$ |
| Empty SDMCs | 0 | $1 \times 10^3$ | $1 \times 10^6$ | $1 \times 10^6$ | $1 \times 10^6$ |

EXAMPLE 59

Prevention of Fata Septicemia Resulting from Mixed Bacterial Peritonitis By Use of SDMC-Entrapped Cefoxitin A model for fatal septicemia resulting from mixed bacterial infections were established in Sprague Dawley rats as described in Example 58. The mortality of each of the treatment groups is reported in Table XV.

TABLE XV

Mortality Due To Fatal Septicemia Results From Mixed Bacterial Peritonitis

| Treatment Groups | Mortality In Animals Following Infection | |
|---|---|---|
| | 4 hours | 72 hours |
| Control | 0 | 9/10 (90%) |
| Cefoxitin im/ip | 0 | 4/10 (40%) |
| SDMC Cefoxitin | 0 | 0 (0%) |

EXAMPLE 60

Reduction of Initial Serum Blood Levels of SDMC-Entrapped Tobramycin Sulfate Following Intraperitoneal Administration To evaluate the effect of SDMC-entrapped tobramycin on serum blood levels, SDMCs were prepared as follows: to a 40 ml solution of 0.95% saline containing 1 gram of tobramycin sulfate was added 3 ml of a 10% (weight per volume) soy lecithin (Alcolec LKE granules). The SDMC-entrapping tobramycins were formed and suspension mixed by swirling. An additional 60 ml of 0.95% saline was added and suspension swirled. Groups of five animals received either 1 ml of saline i.p., 1 ml of aqueous tobramycin sulfate (10 mg) i.p. or SDMC-entrapped tobramycin (10 mg). Animals were bled by caudal vein puncture prior to treatment and at four and twenty-four hours after treatment. Seven levels of tobramycin were determined using standard assay techniques. The results of experiments are shown in Table XVI.

TABLE XVI

Serum Concentrations of Tobramycin Following I.P. Administration

| Experimental Groups | Serum Concentrations (mg/ml) of Tobramycin Time of Administration | | |
|---|---|---|---|
| | 0 | 4 | 24 |
| Control | 0 | 0 | 0 |
| Tobramycin | 0 | 4.5 ± 0.7 | 1.3 ± 0.4 |
| SDMC Tobramycin | 0 | 1.1 ± 0.1 | 1.4 ± 0.1 |

EXAMPLE 61

Stabilization of Methoprene to Ultraviolet Light Degradation by SDMC Encapsulation Methoprene, 90% technical grade, was encapsulated into SDMC in the following manner. To 10 ml of a, soy ecithin (Alcolec X-tra[4]) was added 1 ml of Tween 20 and 1 ml of methoprene. To above mixture was added 5 ml of ethanol and swirled. To the resulting mixture 85 ml of water was added and mixed by swirling. To evaluate ultraviolet light protection by encapsulation of methoprene in SDMCs, standardized flea egg hatching studies were done on environmental surfaces (carpet, 1 ft. × 1 ft. square). Carpet samples received either no treatment, 1% methoprene applied in volatile propellant or methoprene entrapped in SDMCs as prepared above. Flea eggs were applied to the carpet samples and the percent of initial methoprene activity was determined as a function of the percentage of flea eggs which hatched. All carpet samples were exposed to ultraviolet light daily during the study period. The carpet samples were reinfected for three subsequent months. The percentage of methoprene activities for each of the experimental groups are shown in Table XVII.

TABLE XVII

Protection of Methoprene From Ultraviolet Light Degradation

| Experimental Groups | Percentage of Initial Pesticide Activity Time After Application Months | | | |
|---|---|---|---|---|
| | 0 | 1 | 2 | 3 |
| Control | 0 | 0 | 0 | 0 |
| Methoprene | 100 | 0 | 0 | 0 |
| SDMC Methoprene | 100 | 92 | 89 | 90 |

EXAMPLE 62

Reduction of Odor By Encapsulation of Propetamphos by SDMCs

Propetamphos was encapsulated into SDMCs in the following manner. To a 10 ml of a soy lecithin (10% weight per volume in ethanol) was added 1 ml of Tween 20 and 1 ml of propetamphos. To the above mixture was added 90 ml of water and mixed by swirling. A noticeable reduction in offensive odor was observed when compared to equal amounts of propetamphos in ethanol above.

EXAMPLE 63

SDMC Containing Retinoic Acid

A sample of 100 mg of soy lecithin was solubilized at room temperature with 30 mg of retinoic acid in ethanol. One ml of water was added to the solution which resulted in a turbid (cloudy) suspension. Three ml of absolute ethanol was added to the suspension to yield an optically clear solution. SDMCs were formed by dilution of 1 ml of final solution into 10 ml of aqueous solution.

I claim:

1. A method for making a solvent dilution microcarrier vehicle comprising the steps of:
   (a) solubilizing an amphipathic material and a passenger molecule in a first quantity of a non-aqueous solvent appropriate to solubilize both the amphipathic material and the passenger molecule to form a first solution;
   (b) adding a first quantity of water to said first solution to form a turbid suspension;
   (c) adding a second quantity of an appropriate non-aqueous solvent to said turbid suspension in a sufficient amount to cause a second solution to form, said second solution characterized by having optical clarity at room temperature and being monophasic at room temperature; and
   (d) mixing said second solution with air or a second quantity of water sufficient to organize said second solution into a plurality of solvent dilution microcarrier vehicles encapsulating said passenger molecule, each of said solvent dilution microcarrier vehicles in said plurality being of substantially the same size.

2. The method of claim 1, wherein said first quantity of water is from about 4:1 (first quantity of non-aqueous solvent to first quantity of water) to about 10:1 (first quantity of non-aqueous solvent to first quantity of water).

3. The method of claim 1 wherein said second quantity of non-aqueous solvent is from about 15:1 (second quantity of non-aqueous solvent to first quantity of water) to about 100:1 (second quantity of non-aqueous solvent to first quantity of water).

4. The method of claim 1 wherein said passenger molecule is selected from the group consisting of antimicrobials, anti-inflammatories, anti-parasitics, dyes, radio labels, radio-opaque compounds, fluorescent compounds, immunomodulating compounds, peptides, proteins, glycoproteins, lipoproteins, hormones, neurotransmitters, tumorocidal agents, growth factors, toxins, analgesics, anesthetics, monosaccharides, polysaccharides, narcotics, catalysts and enzymes.

5. The method of claim 1 wherein said passenger molecule is lipid-soluble.

6. The method of claim 1 wherein said amphipathic material comprises at least one phospholipid.

7. The method of claim 1, wherein said second solution is mixed with air by aerosolizing.

8. The method of claim 1, wherein said second solution is mixed with water by adding a quantity of said second solution to water thereby causing immediate formation of solvent dilution microcarrier vehicles.

9. The method of claims 1, 7 or 8, wherein said plurality contains solvent dilution microcarrier vehicles ranging from 100 to 300 nanometers in diameter.

10. A method for making a solvent dilution microcarrier vehicle comprising the steps of:
 (a) solubilizing an amphipathic material and a passenger molecule in a first quantity of a non-aqueous solvent appropriate to solubilize both the amphipathic material and the passenger molecule to form a first solution;
 (b) adding a quantity of water to said first solution to form a turbid suspension;
 (c) adding a second quantity of an appropriate non-aqueous solvent to said turbid suspension in a sufficient amount to cause a second solution to form, said second solution characterized by having optical clarity at room temperature and being monophasic at room temperature;
 (d) applying said second solution to a surface and allowing said second solution to dry on said surface; and
 (e) rehydrating said surface to form solvent dilution microcarrier vehicles.

11. A method for making a solvent dilution microcarrier vehicle comprising the steps of:
 (a) solubilizing an amphipathic material and a passenger molecule in a first quantity of a non-aqueous solvent to form a first solution;
 (b) adding a first quantity of water to said first solution to form a turbid suspension;
 (c) adding a second quantity of an appropriate non-aqueous solvent to said turbid suspension in a sufficient amount to cause a second solution to form, said second solution characterized by having optical clarity at room temperature and being monophasic at room temperature; and
 (d) diluting an aliquot of said second solution in a second quantity of water in a ratio from about 1:5 to about 1:100 to form solvent dilution microcarrier vehicles.

12. The method according to claim 11 wherein said second solution is diluted in a ratio of from about 1 to about 10.

13. A method for forming a solvent dilution microcarrier vehicle comprising the steps of:
 (a) solubilizing an amphipathic material and a passenger molecule in a first quantity of a non-aqueous solvent appropriate to solubilize both the amphipathic material and the passenger molecule to form a first solution;
 (b) adding a quantity of water to said first solution to form a turbid suspension;
 (c) adding a second quantity of an appropriate non-aqueous solvent to said turbid suspension in a sufficient amount to cause a second solution to form, said second solution characterized by having optical clarity at room temperature and being monophasic at room temperature; and
 (d) aerosolizing said second solution by mixing it with air to form solvent dilution microcarrier vehicles.

14. The method according to claim 13 wherein said second solution is mixed with air by spraying through a conventional sprayer.

* * * * *

UNITED STATES PATENT AND TRADEMARK OFFICE
CERTIFICATE OF CORRECTION

PATENT NO. : 5,269,979
DATED : December 14, 1993
INVENTOR(S) : Michael W. Fountain It is certified that error appears in the above-identified patent and that said Letters Patent is hereby corrected as shown below:

Column 2, line 60, change "non-flammable-," to --non-flammable,--.

Column 3, line 59, change "impregnated-" to --impregnated--.

Column 4, line 45, change "hydrophili" to --hydrophilic--.

Column 5, line 23, change "1100 mg" to --100 mg--.

Column 5, line 40, change "SMCs" to --SDMCs--.

Column 5, line 66, after "sample", insert --of--.

Column 8, line 64, after "EXAMPLE", change "2" to --26--.

Column 10, line 20, change "0.1 O.D." to --0.1 O.D.--.

Column 10, line 64, change "NM4A" to --NM4AM--.

Column 15, line 36, after "as above", insert --.--.

Column 15, line 37, change "collected-after" to --collected after--.

Column 17, line 11, change "antimicrobial-assay" to --antimicrobial assay--.

UNITED STATES PATENT AND TRADEMARK OFFICE
CERTIFICATE OF CORRECTION

PATENT NO. : 5,269,979
DATED : December 14, 1993
INVENTOR(S) : Michael W. Fountain It is certified that error appears in the above-identified patent and that said Letters Patent is hereby corrected as shown below:

Column 18, line 40, change "0.45 %m" to --0.45 μm--.

Column 20, line 51, change "Fata" to --Fatal--.

Column 21, line 40, change "a, soy" to --a soy--.

Column 21, line 41, change "ecithin" to --lecithin--.

Signed and Sealed this

Fourteenth Day of June, 1994

Attest:

BRUCE LEHMAN

*Attesting Officer*  *Commissioner of Patents and Trademarks*